(12) United States Patent
Walles

(10) Patent No.: US 6,485,683 B1
(45) Date of Patent: Nov. 26, 2002

(54) HEADQUARTER VEHICLES FOR CHEMICAL BIOLOGICAL NUCLEAR DEFENSE

(76) Inventor: Wilhelm E. Walles, 6648 N. River Rd., Freeland, MI (US) 48623

( * ) Notice: Subject to any disclaimer, the term of this patent is extended or adjusted under 35 U.S.C. 154(b) by 0 days.

(21) Appl. No.: 09/344,330

(22) Filed: Jun. 24, 1999

Related U.S. Application Data

(60) Provisional application No. 60/090,816, filed on Jun. 26, 1998.

(51) Int. Cl.[7] .............. C23K 11/00; C23K 11/04; A61L 9/00; A62B 7/08; B32B 27/42
(52) U.S. Cl. .............. 422/4; 422/1; 422/5; 422/12; 422/120; 422/160; 422/182; 422/292; 89/1.1; 134/94.1; 134/200
(58) Field of Search .............. 422/1, 4, 5, 12, 422/160, 182

(56) References Cited

U.S. PATENT DOCUMENTS

| | | | | |
|---|---|---|---|---|
| 3,915,689 A | * | 10/1975 | Bartlett et al. .............. 75/3 |
| 4,014,978 A | * | 3/1977 | Klein et al. .............. 423/242 |
| 4,251,280 A | * | 2/1981 | Heian .............. 106/100 |
| 4,460,552 A | * | 7/1984 | Zakrzewski .............. 423/210 |
| 5,010,907 A | * | 4/1991 | Henson et al. .............. 134/94 |
| 5,030,437 A | * | 7/1991 | Mahadev et al. .............. 423/576.8 |
| 5,236,390 A | * | 8/1993 | Young .............. 454/95 |
| 5,285,604 A | * | 2/1994 | Carlin .............. 52/79.1 |
| 5,603,909 A | * | 2/1997 | Varner et al. .............. 422/173 |
| 5,616,296 A | * | 4/1997 | Hittner et al. .............. 266/145 |
| 5,803,894 A | * | 9/1998 | Kao et al. .............. 588/257 |

OTHER PUBLICATIONS

Merriam Webster's Collegiate Dictionary Tenth Edition, 1993, pp. 952–953.*

* cited by examiner

Primary Examiner—Robert J. Warden, Sr.
Assistant Examiner—Imad Soubra
(74) Attorney, Agent, or Firm—Christopher John Rudy

(57) ABSTRACT

Pyro sulfuric acid is employed to decontaminate air. Contaminated air is contacted with pyro sulfuric acid in a pyro sulfuric acid system, and released as decontaminated air. The system can be especially useful in a chemical/biological/nuclear defense module.

18 Claims, 2 Drawing Sheets

HEADQUARTER VEHICLES FOR CHEMICAL BIOLOGICAL NUCLEAR DEFENSE

CROSS-REFERENCE

Figure 1:
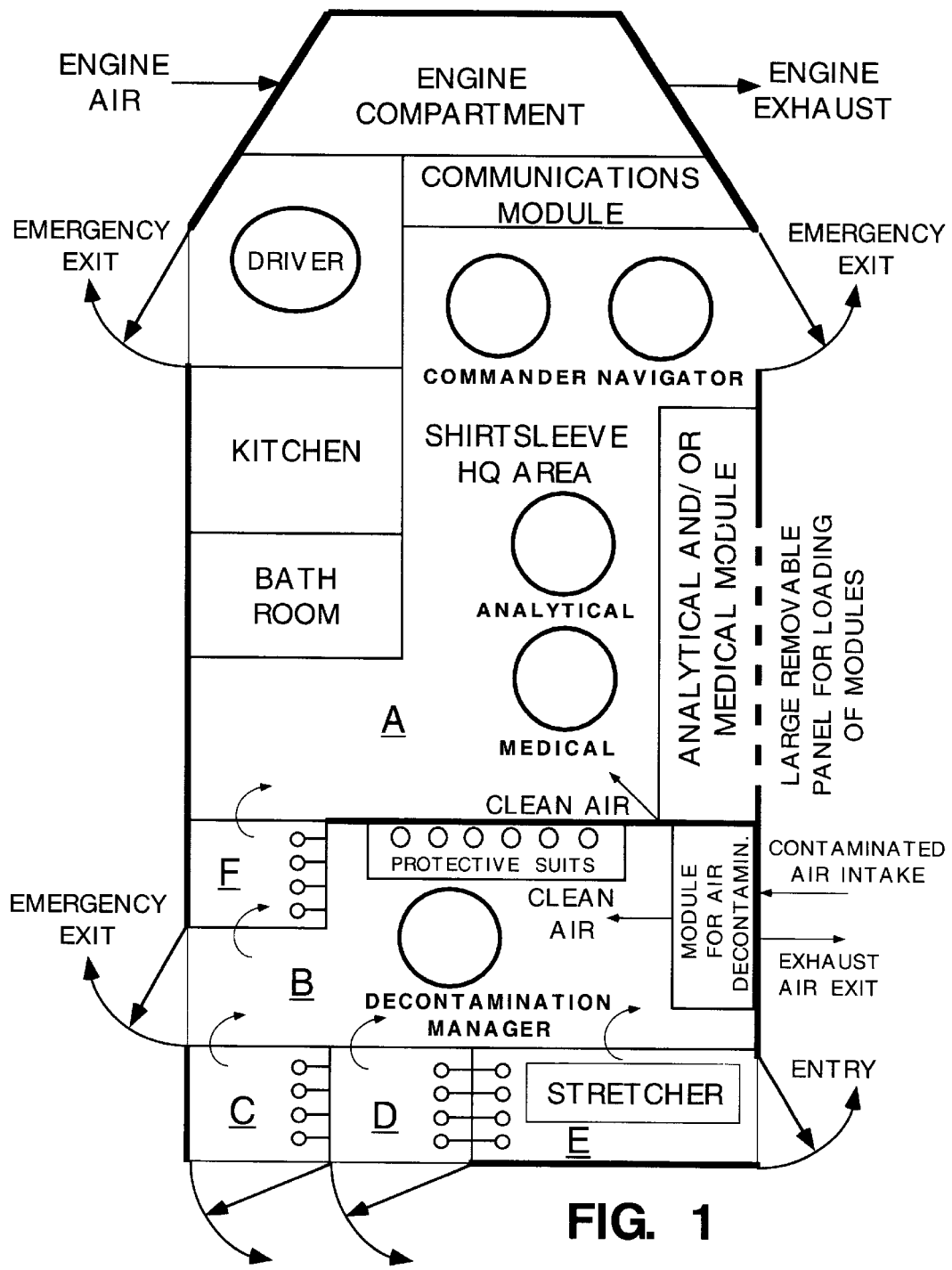
Figure 2:
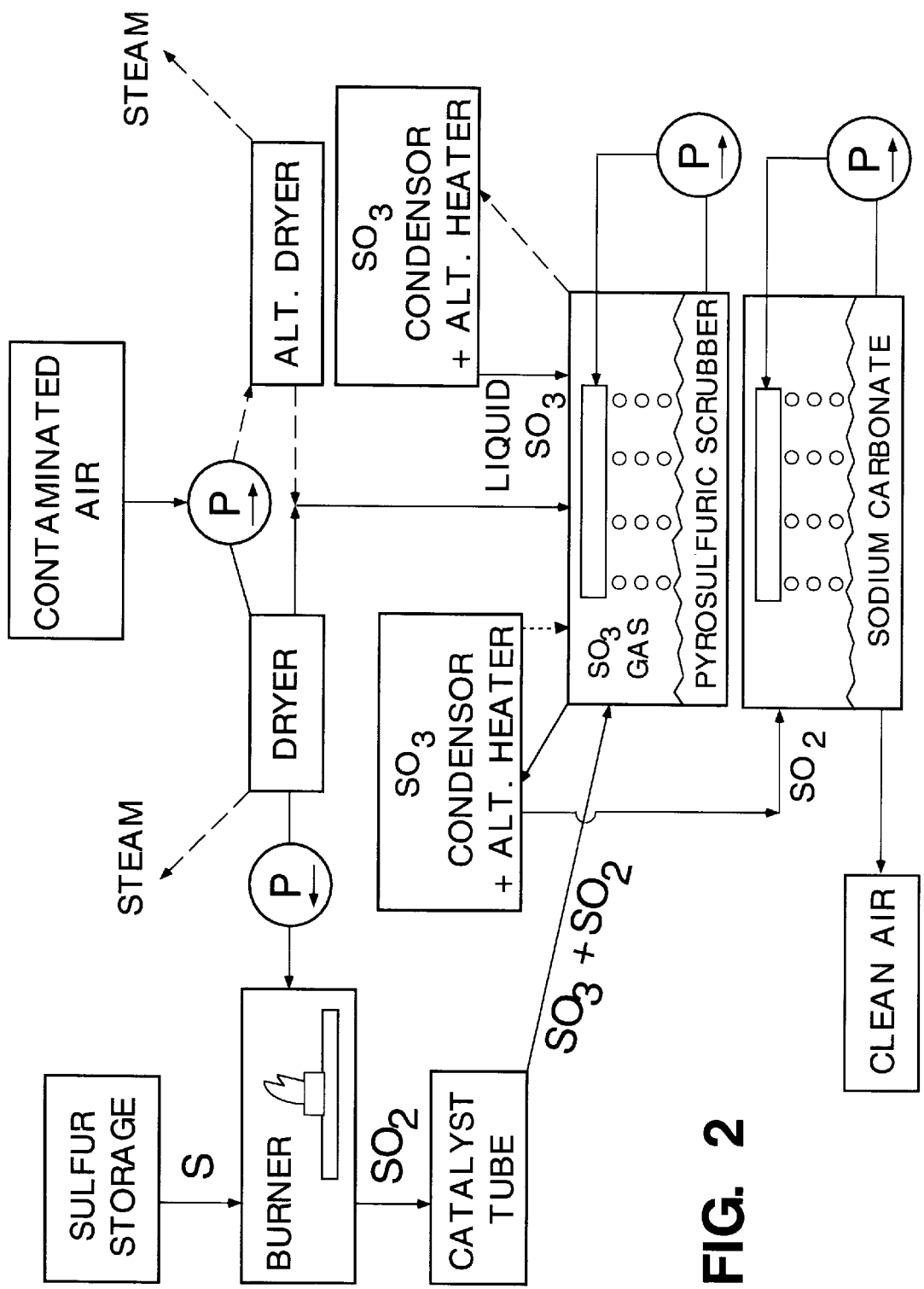

This claims the benefit under 35 USC 119(e) of U.S. provisional patent application Ser. No. 60/090,816, which was filed on Jun. 26, 1998. The specification of that provisional application is incorporated herein by reference.

The threat of exposure on US soil to chemical/biological/nuclear agents is taken seriously by members of Congress. Many government agencies and Armed Forces have taken steps, as summarized herein.

It appears that there is a niche market for several hundred Headquarter (HQ) Vehicles of the same basic design, but customized by agencies with modules for communication, for threat analysis and for medical evacuation.

All have in common a novel system (disclosed hereby) which is capable of providing a shirtsleeve protected vehicle with entry and exit via personal protective suits. This novel system is a large step forward compared with presently used filters and cartridges. It offers simultaneous protection against all three threats: chemical, biological and nuclear, while remaining at top capacity to provide clean air for weeks. The potential customers are listed and tentative specifications for a HQ vehicle. A discussion is given on the technical details of how it works. Finally, a concluding section is set forth, which in part may be likened to a summary of the invention or claim.

The Threat

The US government has expressed strong concern about possible terrorist activity on US soil with chemical, biological and nuclear agents or devices. Extensive measures are in progress on rapid analysis, antidotes and response systems.

There appears to be a critical need for—so far not existing—general purpose headquarter vehicles to be used in areas possibly contaminated with chemical spills or war gases, biological contamination such as anthrax and typhoid, and radioactive contamination.

This HQ vehicle is intended to serve as a safe haven for observation, identification of threatening agents, as a basis for exit and reentry in personal protective suits and evacuation of victims with at least partial decontamination.

The vehicles are intended to be used by the US Army, National Guard, Red Cross, FEMA (Federal Emergency Management Agency), Fire Departments, Emergency Field Hospitals and others. Vehicles have some advantages over helicopters, whose air blasts tend to spread localized contamination sources and fail to protect the pilot.

The threat became reality during the Atlanta Olympic Games with a bomb blast. There is a published report on the various government agencies and US Armed Forces which responded. Accordingly, this 8 page report was studied and used particularly to plan the needs for a general HQ vehicle (see specifications) and to find out who the customers would be.

References:
1. "FBI takes lead in developing counter terrorism effort." Chemical and Engineering Chemistry. Nov. 4, 1996 pages 10 to 16
2. The CBIAC Newsletter regularly covers the field of chemical warfare/Chemical and Biological Defense. Its Information Analysis Center is sponsored by the Defense Technical Information Center (DTIC) which in turn is part of the US Department of Defense.
3. The US Department of Defense regularly issues a list of mainly technical problems which they have clearly identified and have authorized the money for. The SBIR program is the Small Business Innovation Research Program. Dr. Walles has successfully won the competition for several of these projects and gave presentations and demonstrations at SBIR award programs.
4. A most likely source of money to support the HQ vehicle project at the start is the TAT program (Technical Area Tasks) run by the CBIAC (see 2). It regularly reports who got how much money for which project.

Announced events with many people attending are especially vulnerable, such as stadium games and political conventions. Government command centers also are interested in improving their security with HQ vehicles.

Customer for HQ vehicles

The main potential customers appear to be federal, state, local agencies and certain chemical companies, plus US Army, Navy, Marines and Air Force. These diverse customers can be served by small variations on the main design, particularly by not including, but leaving space for communications and analytical modules.

The air decontamination unit covered by this invention should be useful as well for ship borne, airborne, aboard armored vehicles and in Field Hospitals. The nerve gas release in the Tokyo subway, the bombing of the New York Trade Center, the nuclear arms race between India and Pakistan have heightened awareness of terrorist threats.

Presidential Decision Directive 39 of Jun. 22, 1995 lays out US policy on counter terrorism. It gives the FBI lead responsibility for managing the crisis of a credible threat and the FEMA (Federal Emergency Management Agency) the lead in managing the consequences of actual use, both under oversight by the NSC (National Security Council).

However, some 40 federal agencies also have some responsibility. For the 1996 Olympic Games a multi-agency partnership formed the Science and Technology Center (STC) with a fixed HQ and Chem/Bio Response Team which was staffed by 50–70 chemists and biologists borrowed from various federal agencies and headquarters in Atlanta.

The US Army, for rapid identification of chemical warfare agents, set up the Material Command Treaty Laboratory which has a self-contained mobile lab. The US National Guard, eager not to lose mission, is organizing the Homeland Defense Command for greater emphasis on countering poison gas and germ warfare. The US Army also has the Medical Research Institute for Infectious Diseases in Fort Detrick, Md. There also is a US Army Technical Escort for special emergencies and VIP's. The US Navy has the Biological Defense Research Program for identification and verification of biological agents. It is portable and designed to travel quickly anywhere in the world. It is part of the Naval Medical Research Institute. The US Marine Corp has CBIRF, the Chem/Bio Incident Response Force which just received special funding of S10 million. The US Coast Guard now has Coast Guard Strike Teams equipped with bulldozers, backhoes and loaders. The US Air Force has a Chem/Bio Response Team.

The Centers for Disease Control in Atlanta has a Center for Infectious Diseases with close ties to the WHO (World Health Organization) of the United Nations. The US Public Health Service concentrates on treating casualties. Nuclear threats are addressed by the US Dept. of Energy. It has the Forensic Science Center at the Lawrence Livermore National Laboratory.

The EPA (Environmental Protection Agency) has the NEIC (National Enforcement Investigations Center) in Denver, Colo. for identification of hazardous materials. It also has an Emergency Response and Removal Branch which can field a mobile monitoring laboratory. It can drive through a hazardous plume and monitor for poisons. It also has a vehicle with a suite of real time instruments. The NEIC is training 11 of its experts to fit into the Multi-Agency Task Force on Ecoterrorism. The EPA also has a counter terrorism unit called the National Incidents Coordination Team.

The FBI (Federal Bureau of Investigation) sees itself as a "systems integrator" and has chemical and biological counter terrorism experience. It has a Laboratory Division and an Evidence Response Team.

The Central Intelligence Agency and the US Secret Service maintain certain interest, activities and capabilities. Among legislators the highly regarded Defense overseer Senator Sam Nunn has proposed special protection for the most populous 120 US cities. Together with Senator Richard Lugar (R-Ind.) and Senator Pete V. Domenici (R-NM) they recently gave the Pentagon an extra $144 million for response to nuclear/chemical/biological/radiological emergencies. On May 22, 1998 the US President ordered stockpiling of antibiotics and vaccines for civilian protection against biological warfare.

In April 1998 $800,000 was awarded to a small company by DARPA (Defense Advanced Research Projects Agency for vaccine development against bio warfare. The Pentagon has created a new Joint Program Office for Biological Defense in Arlington, Va. It was funded with $1400 million for passive defenses against bio weapons and is managed by the US Army under direct control by the JCS (Joint Chiefs of Staff). The US Army has now set up a new command, the Chemical and Biological Defense Command APG (Maryland).

The Battelle Research Institute operates via its Battelle Edgewood Operations the US Army Edgewood Research, Development and Engineering Center.

Thus, there appear to be agencies eager to conquer part of the new missions, and others concerned about losing mission.

It appears worthwhile to invite the various government and state agencies to participate in a meeting set up to specifically address the specifications for a novel HQ vehicle and to their interest in purchasing one or more.

Announcing the intent to build a series of 100 of these vehicles with greatly improved capabilities may secure their attention and cooperation.

Co-sponsors for such a meeting may be the FBI, DARPA, FEMA, CBIAC, and others, see above.

HQ Vehicle Specifications

The challenge to private industry is to come up with a design which permits the customers with different needs to customize, while sticking to a uniform design. Thus, communications equipment and portable analytical gear are not part of the specs, but space is reserved for them plus an extra large access door and extra electrical power for their modules.

Thus, multiple missions can be accommodated, such as
threat analysis with special equipment
people rescue with medical specialists
command headquarters
special fighting capability Listed specifications are tentative and can be modified via discussion with customers:
1. Maintain slight over-pressure to prevent entry of threat agents into the sealed HQ vehicle.
2. Be self-contained as far as breathing air: 1 month (or 1 week?).
3. Fuel for 1 week, food for 1 week.
4. 1000 mile range per fuel tank.
5. Decontamination capability for 1 month with 200 re-entries.
6. Accommodate 5–10 personnel.
7. Storage for 20 exit personal protective gear; gear itself not included, as agencies have their own.
8. Large door to permit loading of communications module and specialized analytical modules or medical supplies in a module.
9. Air purification system fully automatic, good for 1 month in the field, fool proof.
10. Provide its main mission to provide a shirtsleeve HQ protected from moderate outside chem/bio/nuclear threat and permitting exit and re-entry for people with personal protective suits during threats.
11. Provide 4 simultaneous re-entry cubicles with full decontamination, or as variant 2 simultaneous re-entry cubicles plus 1 stretcher re-entry of double size.
12. Provide extra HQ shirtsleeve protection by having a separate area for donning and storing protective suits and providing emergency rapid contaminated entry bypassing the slow but secure re-entry cubicles. Have an extra cubicle between the shirtsleeve and protective suit area.
13. Carry the novel pyro sulfuric acid type equipment which works without filters, can handle all three threats (chem/bio/nuclear) simultaneously with 1 month fully automatic service.
14. Equip the re-entry, one person cubicles with multiple decontamination faucets and gear for:
ultraviolet light
ozone
pyro sulfuric system
diluted bleach or peroxide
bicarbonate in water
dry, clean breathing air
slight over pressure and leak tight A floor plan for a HQ vehicle with the above specifications is given in FIG. I.

Compartment A is the shirtsleeve environment and has the driver, commander, navigator in front of communication gear and threat analyzer specialist with analytical equipment. Compartment A also has the kitchen and bathroom. It receives clean air from the pyro sulfuric module, free from chem/bio/nuclear contamination. It also has a large removable panel or extra wide door for loading of communications, analytical and/or medical modules prior to a mission. There is an emergency-only driver exit and a door to compartment B, as well as an emergency exit next to the navigator.

Compartment B is run by the Decontamination Manager. It permits donning the personal protection suits. To get from B to A one passes through a decontamination cubicle, not activated under normal conditions. However, if compartment B is compromised in any way, the cubicle permits entry into A only after decontamination. Compartment B is connected to the outside via 2 identical one person cubicles C and D, plus a two person double size cubicle E which can hold a person on a stretcher with one or two attendants. This permits exit and re-entry by several people simultaneously and with people needing assistance.

Under emergency conditions people can use the direct outside door to get in or out, compromising B but leaving A secure. The cubicles are outfitted with multiple decontamination faucets and gear providing:
Ultraviolet lights to sterilize bacteria
ozonized air to provide sterilizing gas
Clean Air diluted bleach water with sodium bicarbonate neutralizer pyro sulfuric system. This permits persons in a personal protection suit to have their suit outside treated with sulfonation gas to decontaminate chem, bio and nuclear threats, after which bicarbonate spray neutralizes all, so that the person can take off the suit while still in the cubicle, then open the sliding door into compartment B. The pyro sulfuric system does not work for people without the suit. In that case diluted bleach, ozonized air and UV light and bicarbonate provide choices, such as needed for stretcher victims and other rescued people.

Again, compartment B can admit people directly through the outside door without compromising A. The decontamination manager in B can observe all cubicles via glass sliding doors and can give instructions and permission to enter B via the electrically controlled doors. Thus, the cubicles can provide everything from just a shower to various decontamination protocols.

Compartment B also houses the pyro sulfuric air cleaning unit, described in more detail below.

Modes of Operation

Switches need to be provided for the following modes of operation:

All off

Standby

Mild threat

Severe threat

Maintenance

This is to be able to provide a clean air turn over of the whole internal vehicle volume in 1 hour, 5 hours, or 10 hours, as needed.

How does it work? Chemistry and Physics.

Chemistry and Physics of Threats.

The threats come, as far as chemistry and physics, in the following physical forms:

gases, small molecules of war gases, which immediately get into the lungs upon breathing and which pass through filters (unless chemically impregnated or carbon-type absorbers which quickly are over burdened).

Ultra small particles and fine dust of nuclear fallout carried far from the source and coming down with rain which, after evaporation, leaves radio active dust. The Chernobyl nuclear accident left a plume of this type over Russia, Poland and Sweden. The radio activity is absorbed in the lungs as particles up to 1–2 micrometer are not exhaled.

Particles of—or with—bacteria and virus, lived and died with toxins, such as anthrax, ricin, flue, etc.

Normal larger dust particles contaminated with the above chemical, biological and nuclear species.

Aerosols, as droplets from warfare munitions either coated or uncoated. Protection against all of these is commonly provided by cartridges with absorbers, such as activated charcoal and filters laden with chemicals. These all have limited capacity and it is difficult to know whether they are almost exhausted. They have to be changed frequently.

Thus, the present invention, as a truly novel system, offers protection against all the above threats remaining continuously at top capacity and capable of running a whole month fully automatic, protecting the whole HQ vehicle including the cubicles for entry and exit.

Also the decontamination of the outside of personal protective suits, all without producing the voluminous waste of filters and cartridges. In summary the novel system has as capabilities:

1. Detoxify and neutralize all known chemical warfare agents and all biological toxins and germs.
2. Rapidly catch fine radioactive dust and suspend it in the liquid part of pyro sulfuric acid.
3. Insure survivability of the HQ vehicles under a wide variety of threats.
4. Permit rapid reuse of expensive personal protective clothing.

Why is the pyro sulfuric system so unique?

The system mixes into the air to be decontaminated 10–30% sulfur trioxide gas which is a very potent oxidizer and sulfonator. Its liquid part scrubs out all threat agents providing constant same high quality of treatment. The gas, containing air loaded with sulfur trioxide, passes a cooler which condenses and polymerizes it, leaving air with only a trace of sulfur oxides. Next, a bicarbonate scrubber removes all sulfur oxides, providing the highest quality of clean air.

The condensed $SO_3$ can automatically be reused in the system with a minimal amount on the premises as it is synthesized on demand from yellow sulfur bricks. Thus, the only chemicals consumed on board are yellow sulfur and bicarbonate (baking powder).

This is the technical basis why a HQ vehicle with the system can run on automatic for a month or more.

Chemistry and Physics of the actions of pyro sulfuric acid.

The absorber system of pyro sulfuric acid contains a gas phase in thermal equilibrium with a liquid, written as

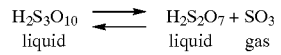

The detoxification chamber is a steel container of 2–5 gallon, partially filled with ceramic saddles. Liquid from it continuously drains into a pump which returns it to the top. Contaminated air enters the vessel, mixes with the 10–30% $SO_3$ and contacts the scrubbing liquid.

Thus, this simple heart of the system circulates 24 hours a day when engaged, consuming only electricity and under no-load produces no waste. Therefore, it can be engaged in about one second by flipping a switch and turned off in the same short time, no problem when switched on and off many times.

Action upon threat agents

In the action chamber the $SO_3$ gas attacks virus and bacteria instantly. It forms sulfuric acid on and inside the cell wall which instantly kills them.

Proteins and carbohydrates contain chemical groupings

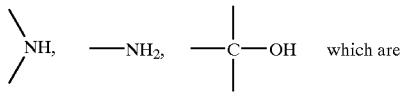

immediately converted to their sulfuric acids:

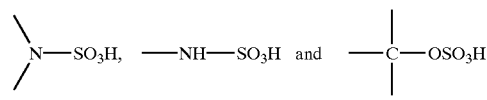

In the liquid part of the chamber a slower reaction takes place in which all organic matter gets converted to $CO_2$ gas and to $N_2$ gas.

For example, glucose: $C_6H_{12}O_6$ $C_6H_{12}O_6 + 18\ SO_3 \rightarrow 6\ CO_2 + 6\ H_2SO_4 + 12\ SO_2$ All chemical threat war gases are converted instantly to their sulfonic acids, such

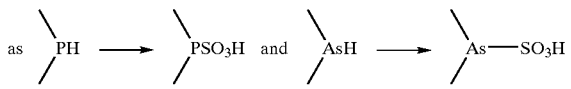

These sulfonic acids are no longer volatile, therefore dissolve in the liquid pyro sulfuric acid in which they are further converted to $H_3PO_4$ for the phosphorus containing agent and to $H_3AsO_4$ for the arsenials.

Radioactive dust particles such as heavy metal isotope oxides, get converted to their sulfates and remain dissolved or suspended in the pyro sulfuric acid.

In FIG. II is shown schematically how clean air emerges.

In Step 1 contaminated air passes through one column of a standard air dryer. The Absorber column is moisture saturated in a few minutes, then switches to a second column while the first is regenerated via heating. The moisture exits as steam to the outside air and may contain some threat agent.

In Step 2 the dry contaminated air enters the pyro sulfuric acid scrubber, as described above.

In Step 3 decontaminated gas with a trace of $CO_2$ and some sulfur oxides is cooled, which condenses and polymerizes virtually all $SO_3$, but not $SO_2$.

In Step 4 A sodium carbonate scrubber removes the last traces of $SO_3$, $SO_2$ and some $CO_2$, plus adds moisture. Thus, purified clean air emerges to maintain the HQ atmosphere in top shape. If a threat agent is involved (see equation) for glucose+$SO_3$, the chemical reaction produces $SO_2$, $CO_2$ and $H_2SO_4$. Thus, $SO_3$ is being depleted.

In order to make $SO_3$ out of sulfur, in Step 5 a sulfur tablet is automatically dumped in a sulfur burner tray, where it is melted electrically and lighted automatically, causing it to burn, to $SO_2$ using some of the dry air via a pump, creating some extra pressure.

In Step 6 the air containing $SO_2$ enters a catalyst tube with $V_2O_5$, vanadium pentoxide, and is heated electrically. Here $SO_2$ with excess dry air is further oxidized to $SO_3$ and passed into the pyro sulfuric scrubber where it replaces the lost $SO_3$. Any unreacted $SO_2$ goes on and is absorbed as in step 4.

Proper sensors and a process computer steer steps 1 through 5. For simplicity values, sensors and other details are not shown in FIG. II.

Thus the module cleans up contaminated air while maintaining top quality. A 1–2 hour monthly maintenance assures continuing availability. The dimensions of the module are about 2'×4' and 7' high, for an illustrative example.

The amount of air to be treated is rather modest, as it has to replace air lost due to leaks in the air seal of the HQ vehicle plus losses resulting from cubicle air losses during exit or entry, plus a healthy reserve for unforeseen emergencies and, of course, human consumption. There is only a small amount of pyro sulfuric acid on the premises.

Maintenance

A small addition, not shown in FIG. II, provides that during the monthly maintenance no smoky pyro sulfuric acid has to be handled or drained, but only non-smoking concentrated sulfuric acid. The latter is immediately placed in a lime neutralizer, leaving non toxic, non hazardous waste. During operation the sodium carbonate solution in water is slowly converted to mostly sodium sulfite and sodium sulfate in water. During monthly maintenance, this liquid is drained and new sodium carbonate solution placed in the scrubber. Thus, maintenance is fast and simple.

The HQ vehicle can be, as illustrated in FIG. I, self-propelled. It should be mounted on an appropriate chassis, to include those with tracked and/or wheeled propulsion or even a floating body such as a boat or barge. As an alernative, the HQ vechile may be towed, for example, as a trailer.

Conclusion, Recapitulation, and Summarization

The present invention is thus provided hereby. Numerous and sundry adaptations and modifications can be effected within its spirit, and parts thereof may be used with or without regard to others. A recapitulation and encapsulation whereof, in general, follows: A method and apparatus to clean up air which is contaminated with chemical, biological or nuclear species, such as needed for sustaining the air in breathable conditions for people in headquarters for observation, analysis or people evacuation, the headquarters being on a vehicle, on a ship or an airplane, the method being that of first drying the contaminated air, second admixing it with 1–40% sulfur trioxide ($SO_3$) gas and forcing it into close contact with liquid pyro sulfuric acid, which gas and liquid chemically react with and alter all living bacteria and virus and all known war gases and trap radioactive isotopes of heavy metals in the liquid portion of the pyro sulfuric acid, where all organics are sulfonated and further oxidized to $CO_2$ and where simultaneously sulfur dioxide ($SO_2$) gas is formed, while heavy metal oxides are converted to their sulfates and dissolved or suspended in the pyro sulfuric acid, third cooling the existing air containing only $SO_2$ and $SO_3$ as extra components, which cooling condenses and polymerizes only $SO_3$ and fourth causing the air containing as extra components $SO_2$ and a trace of $SO_3$ and forcing it in close contact with water in which sodium (or other) carbonate is dissolved, from which emerges pure breathable air, while the condensed $SO_3$ is melted and returned to the pyro sulfuric acid, and the consumed $SO_3$ is replenished by burning sulfur to $SO_2$ and further catalytically to the condensed $SO_3$ is melted and returned to the pyro sulfuric acid, and the consumed $SO_3$ is replenished by burning sulfur to $SO_2$ and further catalytically to $SO_3$, all of this done in an integrated and interconnected apparatus consisting mainly of a pressurizing pump for the incoming contaminated air, a dryer of adsorptive type, a pyro sulfuric acid scrubber, two condensers with alternative heaters to remove $SO_3$ by cooling and cause it to liquefy by heating, after which it flows into the scrubber with pyro sulfuric acid, a scrubber with sodium carbonate solution, while the consumed $SO_3$ is replaced by a dispenser of elemental sulfur into a sulfur burner, followed by a hot tube filled with oxidation catalyst such as vanadium pentoxide, which tube is connected to the pyro sulfuric acid scrubber.

In summary, included hereby are the following embodiments of the present invention:

A) A module for chemical/biological/nuclear defense comprising a hollow housing having an interior and at least one wall enclosing the interior; a doorway in at least one wall of the at least one wall enclosing the interior, through which personnel can pass to or from the interior from or to outside the housing; and an air decontamination system including a pyro sulfuric acid system.

B) The module of embodiment A, which is mobile.

C) The module of embodiment B, which is self-propelled.

D) The module of embodiment C, which is an HQ vehicle.

E) An air decontaminater comprising a hollow vessel; intake and exit openings in the vessel, said intake opening for release of decontaminated air; and, within the vessel and such that said intake and exit openings are in communication, an air decontamination system including a pyro sulfuric acid system.

F) A method for decontamination of contaminated air, said method comprising:
providing an air decontaminater including a hollow vessel; intake and exit openings in the vessel, said intake opening for entry of contaminated air and said exit opening for release of decontaminated air; and, within the vessel and such that said intake and exit openings are in communication, an air decontamination system including a pyro sulfuric acid system;
providing contaminated air to said entry opening whereby said contaminated air comes into contact with at least said pyro sulfuric acid system; and
releasing decontaminated air from said exit opening.

The literal claim scope of the invention is particularly pointed out and distinctly claimed as follows.

I claim:

1. A module for chemical/biological/nuclear defense comprising a hollow housing having an interior and at least one wall enclosing the interior; a doorway in at least one wall of the at least one wall enclosing the interior, through which personnel can pass to or from the interior from or to outside the housing; and an air decontamination system including a pyro sulfuric acid system, which has pyro sulfuric acid for scrubbing a threat agent from the air, a sulfur trioxide condenser, and a bicarbonate/carbonate scrubber.

2. The module of claim 1, which is mobile.

3. The module of claim 2, wherein the bicarbonate/carbonate scrubber includes a dissolved aqueous carbonate.

4. The module of claim 2, which is self-propelled.

5. The module of claim 4, wherein the bicarbonate/carbonate scrubber includes a dissolved aqueous carbonate.

6. The module of claim 3, which is a headquarters vehicle.

7. The module of claim 6, wherein the bicarbonate/carbonate scrubber includes a dissolved aqueous carbonate.

8. The module of claim 1, wherein the bicarbonate/carbonate scrubber includes a dissolved aqueous carbonate.

9. An air decontaminater comprising a hollow vessel; intake and exit openings in the vessel, said intake opening for intake of contaminated air and said exit opening for release of decontaminated air; and, within the vessel and such that said intake and exit openings are in communication, an air decontamination system including pyro sulfuric acid; and further, in communication with the vessel, a sulfur trioxide condenser; and further, in communication with the condenser, a bicarbonate/carbonate scrubber.

10. The air decontaminater of claim 9, wherein the bicarbonate/carbonate scrubber includes a dissolved aqueous carbonate.

11. The method for decontamination of contaminated air, said method comprising:
providing an air decontaminater including a hollow vessel; intake and exit openings in the vessel, said intake opening for entry of contaminated air and said exit opening for release of decontaminated air; and, within the vessel and such that said intake and exit openings are in communication, an air decontamination system including pyro sulfuric acid; and further, in communication with the vessel, a sulfur trioxide condenser; and further, in communication with the condenser, a bicarbonate/carbonate scrubber;
providing contaminated air to said entry opening whereby said contaminated air comes into contact with said pyro sulfuric acid;
releasing decontaminated air from said exit opening;
passing the decontaminated air through said condenser; and
passing the decontaminated air through said scrubber.

12. The method of claim 11, wherein pyro sulfuric acid is obtained from yellow sulfur.

13. The method of claim 10, wherein the bicarbonate/carbonate scrubber includes a dissolved aqueous carbonate.

14. A module for chemical/biological/nuclear defense comprising a hollow housing having an interior and at least one wall enclosing the interior; a doorway in at least one wall of the at least one wall enclosing the interior, through which personnel can pass to or from the interior from or to outside the housing; and an air decontamination system including a pyro sulfuric acid system.

15. The module of claim 16, which is mobile.

16. The module of claim 15, which is self-propelled.

17. The module of claim 16, which is a headquarters vehicle.

18. An air decontaminater comprising a hollow system; intake and exit openings in the hollow system, said intake opening for intake of a contaminated air and said exit opening for release of a decontaminated air; and, within the hollow system and such that said intake and exit openings are in communication therewith, an air decontamination system including a pyro sulfuric acid system.

* * * * *